United States Patent [19]

Schroeder

[11] Patent Number: 4,677,843

[45] Date of Patent: Jul. 7, 1987

[54] ROLLER OVEN FOR TESTING FLUIDS

[75] Inventor: Royce E. Schroeder, Spring, Tex.

[73] Assignee: OFI Testing Equipment Inc., Houston, Tex.

[21] Appl. No.: 694,024

[22] Filed: Jan. 23, 1985

[51] Int. Cl.[4] .................... G01N 11/00; G01N 25/00; F27B 17/02; F27D 21/02

[52] U.S. Cl. ........................................ 73/54; 219/389; 219/392; 219/494; 366/145; 422/209; 432/112

[58] Field of Search ............... 219/389, 392, 390, 494; 432/112; 422/209, 199, 202; 366/145, 146; 436/2; 73/54, 61.3, 61.4

[56] References Cited

U.S. PATENT DOCUMENTS

| | | | |
|---|---|---|---|
| 1,293,402 | 2/1919 | Giles | 422/209 X |
| 2,521,949 | 9/1950 | Roen | 422/209 X |
| 3,116,680 | 1/1964 | Neumann | 422/209 |
| 3,136,150 | 6/1964 | Young et al. | 73/10 |
| 3,421,432 | 1/1969 | Giepen | 219/392 |

Primary Examiner—Kenneth J. Ramsey
Attorney, Agent, or Firm—Neal J. Mosely

[57] ABSTRACT

An oven for testing fluid samples to determine the effects of temperature and various chemical additives on the rheological, filtration and chemical properties of the sample under simulated circulating conditions comprises an environmental chamber having therein a plurality of motorized roller members which rotatably support a cylindrical enclosure containing a fluid sample. A heating element disposed beneath the rollers heats the chamber to a predetermined temperature which is maintained by a thermostat. An instrumentation and control panel disposed atop the chamber contains a digital thermometer display which eliminates the need to open the oven to check the temperature. A timer contained within the instrumentation and control panel may be preset to start and end the test automatically without having an operator in constant attendance.

13 Claims, 5 Drawing Figures

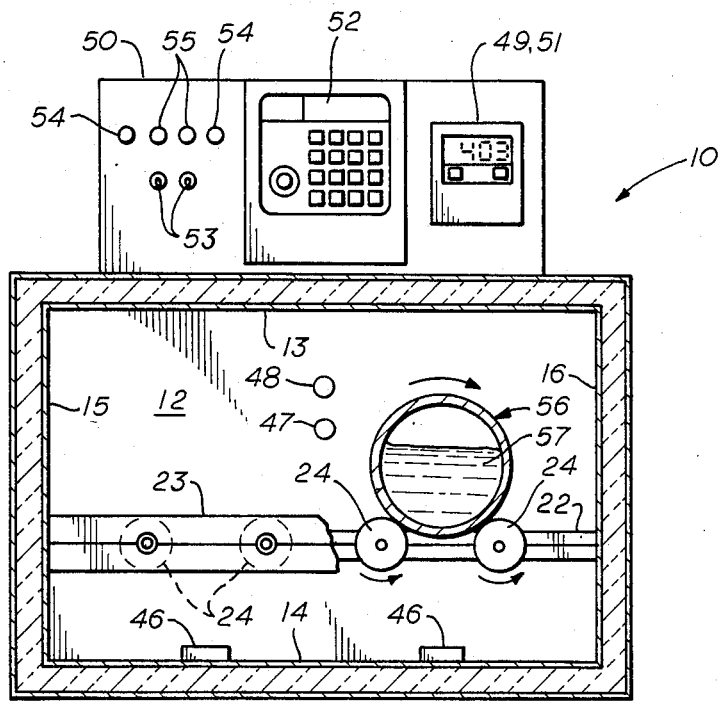
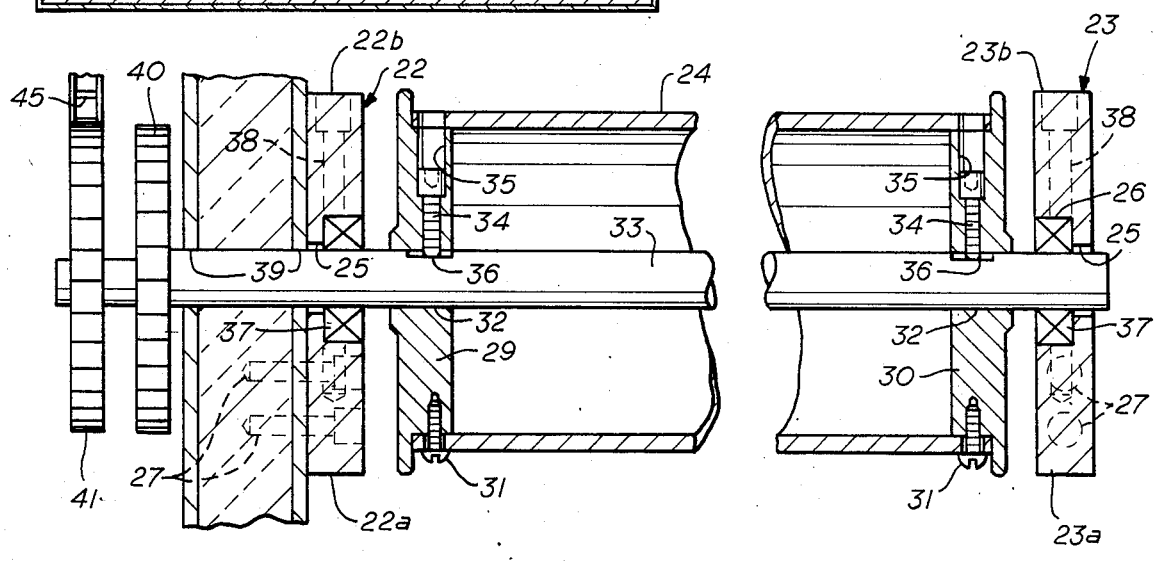
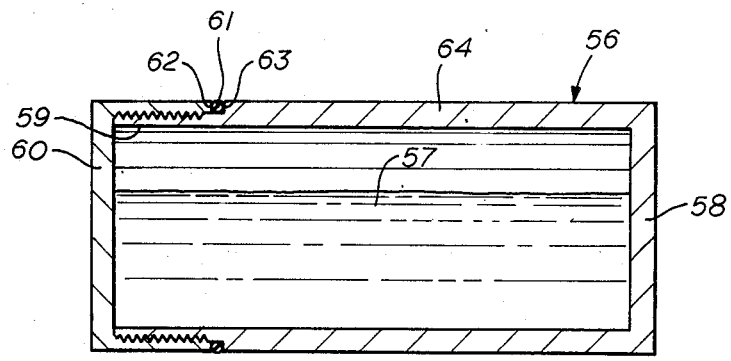
fig.3
fig.4
fig.5

ROLLER OVEN FOR TESTING FLUIDS

BACKGROUND OF THE INVENTION

Field of the Invention

This invention relates generally to test ovens, and more particularly to an oven for testing fluid samples to determine the effects of temperature and various chemical additives on the rheological, filtration and chemical properties of the sample under simulated circulating conditions.

BRIEF DESCRIPTION OF THE PRIOR ART

Several patents which disclose test apparatus for testing various fluids, including fluid, illustrate the prior art which is relevant to this invention.

Beck, U.S. Pat. No. 4,262,521 discloses an environmental test chamber for testing granular epoxy resin samples wherein a sample tube containing a sample of the granular epoxy resin is subjected to temperature and pressure to cause deformation of the sample tube to a lessor or greater degree depending upon whether the epoxy resin is in a granular or plastic state.

Young, U.S. Pat. No. 3,136,150 discloses a closed hollow vessel for testing the lubricity of drilling muds under simulated drilling conditions. The vessel has a port open to relatively low pressure, a sample receiving pallet disposed over the port, a rotating plate which contacts the sample on the pallet to indicate the amount of torque required for rotation. The vessel may be heated and pressurized internally. The apparatus measures the friction existing between a mud cake and a steel surface when subjected to varying temperatures, torsional forces, and differential pressures.

Alekhim et al., U.S. Pat. No. 4,341,115 discloses a method and apparatus for monotoring structural and mechanical properties of fluid. The apparatus comprises a viscosimeter having a driven sensitive element immersed in the fluid and an instrument for measuring the shear strength, having a driven sensitive element immersed in the fluid, both having converters for converting signal supplied from the sensitive elements into signals characterizing, respectively, viscosity and shear strength of the fluid.

Parker et al., U.S. Pat. No. 3,289,467 discloses a process and apparatus for testing fluid characteristics comprising an upright pressure sealed mud vessel having positioned therein a rotatable cylindrical filter head on a hollow shaft extending through the top of the mud vessel, there being passageways in the filter head connecting with an axial bore leading into the hollow shaft. Means are provided on the upper end of the hollow shaft for measuring the amount of filtrate passing through the filter during any selected period of time. An inlet for pressurizing fluid or gas is provided on the top of the mud vessel.

A printed publication entitled "COMPOSITION AND PROPERTIES OF OIL WELL DRILLING FLUIDS", Fourth Edition, by George R. Gray and H. C. H. Darley shows a picture of a laboratory test oven which is apparently owned by National Lead Company. No patent reference is known which describes this test oven and no description or construction or operation is known other than this publication.

The prior art in general, and these patents in particular, do not disclose the present invention of an oven having an environmental chamber having therein a plurality of motorized roller members that rotatably support a cylindrical enclosure containing a fluid sample, a heating element disposed beneath the rollers for heating the chamber to a predetermined temperature, a thermostat to maintain the temperature, and an instrumentation panel disposed atop the chamber which contains a digital thermometer display eliminating the need to open the oven to check the temperature and a timer which may be preset to start and end the test automatically without having an operator in constant attendance.

SUMMARY OF THE INVENTION

It is therefore one object of the present invention to provide an oven for testing fluid samples to determine the effects of temperature and various chemical additives on the rheological, filtration and chemical properties of a fluid sample under simulated circulating conditions.

Another object of this invention is to provide an oven for testing fluid samples which contains a plurality of motorized roller members that rotatably support a cylindrical enclosure containing a fluid sample for simulating circulating conditions.

Another object of this invention is to provide an oven for testing fluid samples having a heating element disposed beneath roller members for heating the oven chamber and fluid sample to a predetermined temperature.

Another object of this invention is to provide an oven for testing fluid samples wherein an instrumentation panel disposed atop the chamber contains a digital thermometer display which eliminates the need to open the oven to check the temperature and a timer contained which may be preset to start and end the test automatically without having an operator in constant attendance.

Other objects of the invention will become apparent from time to time throughout the specification and claims as hereinafter related.

The above noted objects and other objects of the invention are accomplished by an oven having an environmental chamber with a plurality of motorized roller members which rotatably support a cylindrical enclosure containing a fluid sample. A heating element disposed beneath the rollers heats the chamber to a predetermined temperature maintained by a thermostat. An instrumentation and control panel disposed atop the chamber contains a digital thermometer display which eliminates the need to open the oven to check the temperature. A timer contained within the instrumentation and control panel may be preset to start and end the test automatically without having an operator in constant attendance.

BRIEF DESCRIPTION OF THE DRAWINGS

FIG. 3 is a sectional view of the oven taken along line 3—3 of FIG. 1.

FIG. 4 is a view in longitudinal central cross section of one roller member of the oven.

FIG. 5 is a view in longitudinal central cross section of a sealed container for fluid samples.

DESCRIPTION OF THE PREFERRED EMBODIMENT

Figure 1:
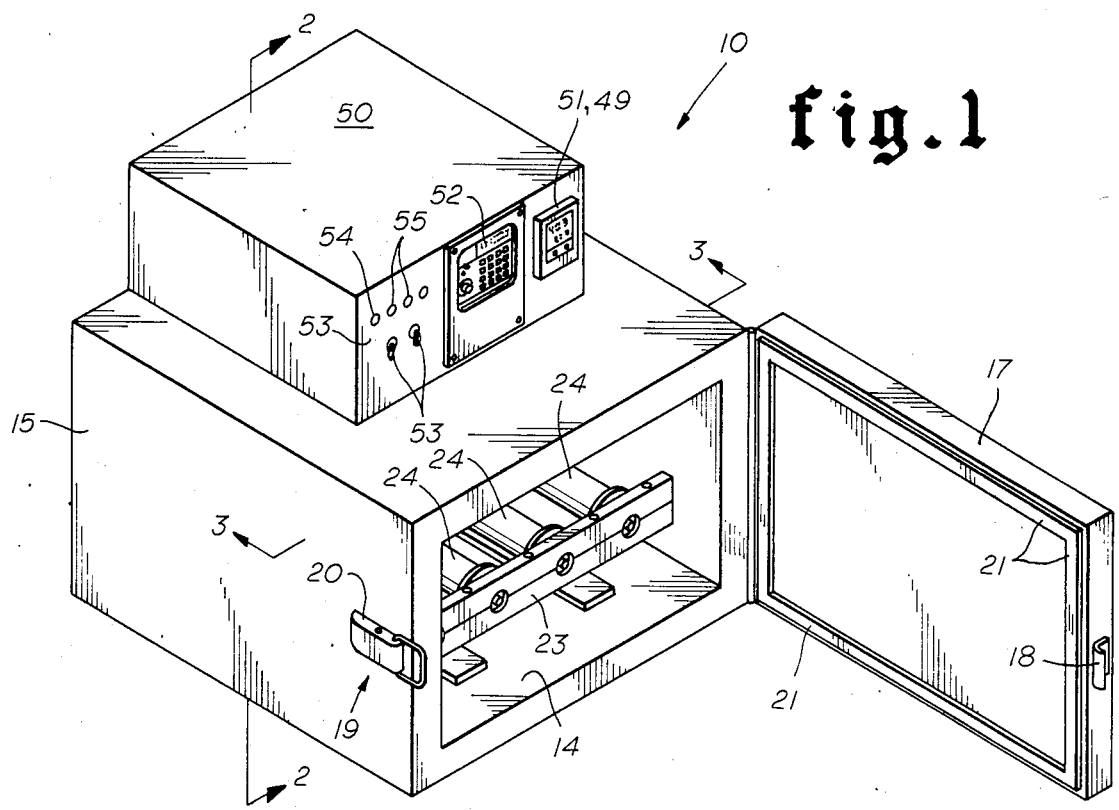
FIG. 1 is an isometric view of a preferred embodiment of this invention comprising an oven for testing the effects of temperature and chemical additives on fluid samples.
Figure 2:
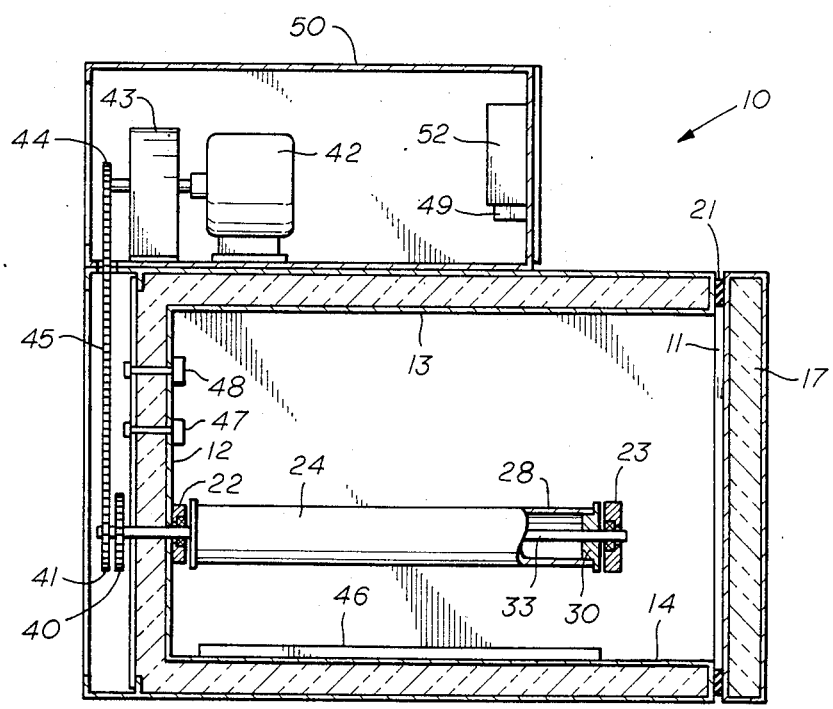
FIG. 2 is a sectional view of the oven taken along line 2—2 of FIG. 1.

Referring to the drawings by numerals of reference, and particularly to FIGS. 1, 2 and 3, there is shown an oven 10 used for testing fluid samples, especially drilling muds, to determine the effects of temperature and various chemical additives on rheological, filtration and chemical properties, particularly viscosity, under simulated circulating conditions. The oven 10 is box-shaped, having an open front 11, a back wall 12, top wall 13, bottom wall 14, and a pair of side walls 15 and 16.

A hinged door 17 has one end attached to one side of the open front 11, as by a piano hinge, and its opposing end supports one component 18 of a toggle latch 19. The other component 20 of the toggle latch 19 is located on the side wall 15. A thermal insulating gasket 21 extends around the periphery of the inner panel of the door 17. Each of the walls and the door are constructed of a blanket of thermally insulating material sandwiched between an interior metal panel and an exterior metal panel. The interior surfaces of the walls form an enclosed environmental test chamber when the door is closed and latched.

A first flat rectangular cross bar 22 is secured to the interior surface of the back wall 12 intermediate the top wall 13 and the bottom wall 14 to extend transversly between the two side walls 15 and 16. A second flat rectangular cross bar 23 is spaced outwardly parallel to the first cross bar 22 and secured to the side walls 15 and 16 as described hereinafter. A plurality of parallel laterally spaced cylindrical roller members 24 are rotatably mounted between the first and second cross bars 22 and 23.

In FIG. 4, it is seen that cross bars 22 and 23 are divided longitudinally into lower segments 22a and 23a, and upper segments 22b and 23b. A series of through bores 25 and counterbores 26 are formed on the dividing line of the upper and lower segments to retain the roller members 24 as described hereinafter. The lower segment 22a is secured to the backwall 12 and the lower segment 23a is secured to the side walls 15 and 16 by cap screws 27.

Each of the rollers 24 comprises an elongated hollow cylindrical drum 28 having flat cylindrical disks 29 and 30 secured in the open ends by screws 31. The disks 29 and 30 have axially aligned central bores 32 which slidably receive an elongated shaft 33. The disks 29 and 30 are secured to the shaft 33 by set screws 34 in a threaded bore 35 extending radially from the central bores 32 to the outer surface of the disks. The set screws 34 are threadably tightened against flats 35 formed on the outer diameter of the shaft 33. The ends of each shaft 33 extend outwardly from the disks 29 and 30.

Special bearings that are not adversely affected by heat and load, such as glass-impregnated, Teflon (tm) bearings 37 are located at each end of the rollers 24 outside the disks 29 and 30 on the shafts 33. Bearings 37 are contained between the upper and lower segments 22a, 22b, and 23a, 23b within the counterbores 26. The bearings 37 are secured in place by turning cap screws 38 threadably mounted in the lower sections 22a and 23a and retained in the upper sections 22b and 23b to pull the upper and lower segments together.

The rear ends of shaft 33 extend through openings 39 in the back wall 12 and each has a chain sprocket 40 mounted thereon adjacent to the outer surface of the back wall 12. Sprockets 40 are operatively interconnected by a chain (not shown) for simultaneous rotary movement. A first drive sprocket 41 is mounted adjacent the chain sprocket on the rearwardly extended end of the outermost shaft.

Referring now to FIGS. 1, 2, and 3, an electric motor 42 powered by a source of electric current (not shown) is mounted on the top of the oven 10. A gear reduction mechanism 43 is coupled to the motor drive shaft and a second drive sprocket 44 extends outwardly therefrom in parallel alignment with the first drive sprocket 41 of the roller sprocket assembly. A chain 45 operatively connects the first and second drive sprockets 41 and 44 whereby rotary motion created by the motor 42 through the gear reduction mechanism 43 is transmitted to the chain and sprocket 40 to simultaneously rotate the rollers 24.

A pair of parallel heating elements 46 are mounted on the bottom wall 14 below the rollers 24. A thermostat 47 interconnected with the heating elements 46 establishes and maintains a predetermined temperature within the oven 10. The sensing component 48 of a digital thermometer 49 is mounted on the back wall 12 of the oven.

A control panel 50 mounted on top of the oven 10 covers the motor 42 and reduction gear mechanism 43. The visual display and control component 51 of the digital thermometer 49, and a seven day timer 52 are contained in the control panel 50. On-off switches 53, indicator lamps 54, and motor controls 55 are disposed on the front of the control panel 50. It should be understood that the control panel also contains wiring and circuitry which is conventional and therefor not shown.

FIGS. 3 and 5 show a sealed enclosure, or container 56 which receives a fluid sample 57. The container 56 is an elongated cup shaped cylindrical member having an enclosed end 58 and an open threaded end 59. A mating threaded cap member 60 is received on the threaded open end 59. A heat resistive gasket 61 is captured between the bottom end 62 of the cap 60 and a radial shoulder 63 formed on the container side wall 64 forms a fluid tight seal around the threads.

OPERATION

The apparatus is used to determine the effects of temperature and chemical additives on rheological, filtration and chemical properties of a fluid sample, such as a drilling mud, under simulated circulating conditions. If chemical additives are being used in the test, they may be added to the fluid sample before or after measurement. The fluid sample is then placed into the container and the cap is sealed.

The heaters are turned on and the thermometer is set to preheat the oven chamber to a predetermined temperature. The container is then placed into the oven chamber on the rollers. The timer is set and the motor is operated to rotate the rollers and the container of fluid for a predetermined length of time at the selected temperature.

The timer may be preset to start and end the test automatically without having an operator in constant attendance, and the the digital thermometer can be read directly from outside the oven, thus eliminating the need to continually open the oven to check temperature.

At the appropriate time, the container is removed from the oven chamber and the sample is again measured to determine the change in rhelolgical, filtration and chemical properties of the fluid sample due to the effect of the temperature and time to which the sample was subjected.

While this invnention has been described fully and completely with special emphasis upon a preferred embodiment, it should be understood that within the scope of the appended claims the invention may be practiced otherwise than as specifically described herein.

I claim:

1. An apparatus for testing fluid samples to determine the effect of temperature and various chemical additives on rheological, filtration and chemical properties under simulated circulating conditions comprising, in combination;

an enclosable emviromental chamber capable of maintaining its interior at a predetermined temperature and having a sealable door member, a cylindrical container having an end opening with a removable cover sealed for receiving a fluid material for testing and removably positioned in said chamber, supporting means for rotatably supporting said fluid container, means for turning said supporting means to rotate said chamber, heating means positioned at the bottom of said chamber underlying said supporting means for heating the interior of said chamber and said fluid, temperature measuring means for measuring the temperature within said chamber, temperature indicating means supported outside said chamber on the top thereof, thermostat means positioned outside said chamber on the tip thereof and cooperative with said heating means for establishing and maintaining a predetermined temperature within said chamber, and a housing exterior to said chamber on the top thereof enclosing said temperature indicating means and said thermostat means for easy access and visibility.

2. An apparatus according to claim 1 including timing means positioned in said housing outside said chamber on the top thereof for adjustably controlling the length of operation of said heating means and said moving means.

3. An apparatus according to claim 1 in which said temperature measuring means has a temperature sensing component within said chamber connected to said temperature indicating means in said housing outside said chamber on the top thereof for indicating the temperature within said chamber.

4. An apparatus according to claim 1 in which said supporting means comprises;

a first flat rectangular cross bar secured to the interior back wall of said chamber and extended transversly between two opposed interior side walls, a second flat rectangular cross bar spaced outwardly from said first cross bar in a parallel relation and secured to same said opposed interior side walls, a plurality of parallel laterally spaced cylindrical roller members rotatably mounted and journaled within and extending between said first and second cross bars, and said turning means comprising means for rotating said rollers to rotate said container.

5. An apparatus according to claim 4 in which; each said roller having a concentric longitudinally extending member which extends through the back wall of said chamber to receive a sprocket member, a chain member interconnecting said sprockets for simultaneous rotary movement, a first drive sprocket member attached to one said longitudinally extending member for receiving rotary motion from said means for moving and transmitting rotary motion to said interconnecting sprockets, and said means for moving said roller members comprises an electric motor having a source of electric current and a second drive sprocket for transmitting rotary motion to said first drive sprocket.

6. An apparatus according to claim 5 further including gear reduction means coupled between said motor and said second drive sprocket.

7. An apparatus according to claim 4 in which said roller members are rotatably mounted within said cross bars on heat resistive bearings.

8. An apparatus according to claim 1 including timing means positioned outside said chamber on the top thereof for adjustably controlling the length of operation of said heating means and said moving means, and said temperature measuring means having a temperature sensing component within said chamber connected to said temperature indicating means outside said chamber on the top thereof for indicating the temperature within said chamber.

9. An apparatus according to claim 1 including timing means positioned outside said chamber on the top thereof for adjustably controlling the length of operation of said heating means and said moving means, said temperature measuring means having a temperature sensing component within said chamber connected to said temperature indicating means outside said chamber on the top thereof for indicating the temperature within said chamber, said supporting means comprising a first flat rectangular cross bar secured to the interior back wall of said chamber and extended transversly between two opposed interior side walls, a second flat rectangular cross bar spaced outwardly from said first cross bar in a parallel relation and secured to same said opposed interior side walls, and a plurality of parallel laterally spaced cylindrical roller members rotatably mounted and journaled within and extending between said first and second cross bars.

10. An apparatus according to claim 1 including timing means positioned outside said chamber in the top thereof for adjustably controlling the length of operation of said heating means and said moving means, said temperature measuring means having a temperature sensing component within said chamber connected to said temperature indicating means outside said chamber on the top thereof for indicating the temperature within said chamber, said supporting means comprising a first flat rectangular cross bar secured to the interior back wall of said chamber and extended transversly between two opposed interior side walls, a second flat rectangular cross bar spaced outwardly from said first cross bar in a parallel relation and secured to same said opposed interior side walls, and a plurality of parallel laterally spaced cylindrical roller members rotatably mounted and journaled within and extending between said first and second cross bars, each said roller member having a concentric longitudinally extending member which extends through the back wall of said chamber to receive a sprocket member, a chain member interconnecting said sprocket for simultaneous rotaray movement, a first drive sprocket member attached to one said longitudinally extending member for receiving rotary motion from said means for moving and transmitting rotary motion to said interconnected sprockets, and said means for moving said roller members comprises an electric motor having a source of electric current and a second drive sprocket for transmitting rotary motion to said first drive sprocket.

11. An apparatus according to claim 1 including timing means positioned outside said chamber on the top thereof for adjustably controlling the length of operation of said heating means and said moving means, said temperature measuring means having a temperature sensing component within said chamber connected to said temperature indicating means outside said chamber on the top thereof for indicating the temperature within said chamber, said supporting means comprising a first flat rectangular cross bar secured to the interior back wall of said chamber and extended transversly between two opposed interor side walls, a second flat rectangular cross bar spaced outwardly from said first cross bar in a parallel relation and secured to same said opposed interior side walls, and a plurality of parallel laterally spaced cylindrical roller members rotatably mounted and journaled within and extending between said first and second cross bars on heat resistive bearings, each said roller member having a concentric longitudinally extending member which extends through the back wall of said chamber to receive a sprocket member, a chain member interconnecting said sprockets for simultaneous rotary movement, a first drive sprocket member attached to one said longitudinally extending member for receiving rotary motion from said means for moving and transmitting rotary motion to said interconnected sprockets, said means for moving said roller members comprises an electric motor having a source of electric current and a second drive sprocket for transmitting rotary motion to said first drive sprocket, and gear reduction means coupled between said motor and said second drive sprocket.

12. A method of testing fluid samples to determine the effects of temperature and chemical additives on rheological, filtration an chemical properties under simulated circulating conditions comprising the steps of;

measuring the rheological, filtration and chemical properties of said fluid sample and placing said sample into a sealed enclosure, preheating an environmental chamber as defined in claim 1 to a predetermined temperature, placing said sealed enclosure into said preheated environmental chamber on rotatable rollers, rotating said rollers and said enclosure for a predetermined length of time at a predetermined temperature, removing said enclosure from said chamber, and measuring the change in rheological, filtration and chemical properties of said fluid sample due to the effect of the temperature and time to which said sample was subjected.

13. A method of testing fluid samples to determine the effects of temperature and chemical additives on rheological, filtration and chemical properties under simulated circulating conditions comprising the steps of;

measuring the rheological, filtration and chemical properties of said fluid sample, adding a selected amount of a chemical additive to the fluid sample and placing said sample into a sealed enclosure, preheating an environmental chamber as defined in claim 1 to a predetermined temperature, placing said sealed enclosure into said preheated environmental chamber on rotatable rollers, rotating said rollers and said enclosure for a predetermined length of time at a predetermined temperature, removing said enclosure from said chamber, and measuring the change in rheological, filtration and chemical properties of said fluid sample due to the effect of the chemical additive and the temperature and time to which said sample was subjected.

* * * * *